United States Patent [19]

Cannon et al.

[11] Patent Number: 5,017,602

[45] Date of Patent: May 21, 1991

[54] ANTAGONISTS OF ORGANOPHOSPHATE-INDUCED TOXICITY

[75] Inventors: Joseph G. Cannon; Ranbir K. Bhatnagar; J. Paul Long, all of Iowa City, Iowa

[73] Assignee: University of Iowa Research Foundation, Iowa City, Iowa

[21] Appl. No.: 392,763

[22] Filed: Aug. 10, 1989

[51] Int. Cl.$^5$ .................. A61K 31/335; C07D 319/06
[52] U.S. Cl. ..................................... 514/452; 549/370
[58] Field of Search ......................... 549/370; 514/452

[56] References Cited

PUBLICATIONS

Cannon et al., J. Med. Chem., 33(2), 577–579 (1990).

*Primary Examiner*—Nicky Chan
*Attorney, Agent, or Firm*—Zarley, McKee, Thomte, Voorhees, & Sease

[57] ABSTRACT

Analogs and congeners of 4,4'-bis-[(1,3-dioxan-2-ylmethyl)aminoacetyl]biphenyl Dimethbromide. The compounds are effective antagonists of paraoxon induced toxicity and antagonized physiological response to certain nerve gas.

9 Claims, No Drawings

ANTAGONISTS OF ORGANOPHOSPHATE-INDUCED TOXICITY

GRANT REFERENCE

The U.S. Government has a nonexclusive, nontransferable, irrevocable paid-up license to practice or have practiced this invention for or on its behalf as provided for by the terms of Contract No. DAMD17-87-C-7113 awarded by the U.S. Department of the Army.

BACKGROUND OF THE INVENTION

It is known that certain compounds produce an organophosphate-induced toxicity both in humans and other mammals. It is known that certain compounds will diminish the level of acetylcholine in nerve terminals by the inhibition of the sodium-dependent high affinity choline uptake mechanism. These compounds such as hemicholinium-3 present a complex spectrum of pharmacological effects, including blockade of neuromuscular transmission. It was, therefore, initially believed that compounds such as hemicholinium may prove useful as nerve terminal blockers for organophosphorous toxicity.

Organophosphorous toxicity produces uncontrolled impulses which move up and down the neurotransmitters and ultimately can cause death. This forms the basis for nerve gas or war gases, such as tabun and sarin, soman. It goes without saying that there is a continuing need for the development of successful antagonists which when administered will render nerve gas harmless.

Another much more common risk that occurs in day-to-day life is the exposure of agricultural employees to highly toxic insecticides and herbicides. Many of these are organophosphorous compounds and will stimulate, although to a lesser degree than war gas, the same symptoms of organophosphate toxicity. Typical examples of such agricultural insecticides would be the trade-marked brands Peraoxon and Parathion.

It is not at all uncommon for farm workers to be exposed to heavy doses of insecticides/herbicides during spring application to cultivated fields. When this occurs, especially if caution is not taken, there is a very real risk of being overcome. This can occur from either inhalation of vapors of the organophosphate insecticide/herbicides, or it can come from absorption directly through the skin, since many of these compounds can be readily absorbed.

It can therefore be seen that there is a real and continuing need to develop antagonists for these agricultural chemicals known to induce organophosphate toxicity. Such antagonists could be administered in a prophylactic way before exposure to the chemicals, or alternatively in a therapeutic treatment way after exposure to the chemicals.

Accordingly, it is a primary objective of the present invention to provide new compounds which have the capability of neutralizing many of the components of organophosphate induced toxicity.

Another objective of the present invention is to provide compounds which can be used as effective blockers for neutralizing components against war gases, such as nerve gas.

Another objective of the present invention is to provide certain compounds which can be used to neutralize or block organophosphate induced toxicity caused by certain insecticides/herbicides.

Another objective of the present invention is to provide compounds which not only have the capability of neutralizing many of the components of organophosphate induced toxicity but which have very high therapeutic indexes, indicating safety in use.

The method and manner of accomplishing each of these objectives, as well as others, will be apparent from the detailed description of the invention which follows hereinafter.

SUMMARY OF THE INVENTION

New compounds which are a series of congeners of hemicholinium-3, in which the 1,4-oxazinium rings of hemicholinium are replaced by pyrrolidine, piperidine, 1,3-dioxane, or 1,4-oxazine rings. Several of these compounds produced blockade of neuromuscular transmission in the rabbit. One compound, a 1,3-dioxane derivative, was an extremely potent antagonist of the brand Paraoxon-induced toxicity in mice, compared with prototypical protective agents physostigmine and pyridostigmine. This compound also exhibited a much more favorable therapeutic ratio than the reference drugs physostigmine and pyridostigmine.

DETAILED DESCRIPTION OF THE INVENTION

Compounds of the present invention have the following general formula:

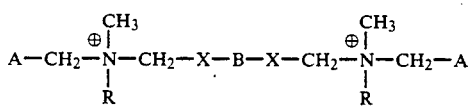

In this formula "A" represents a 5, 6 or 7 member heterocyclic oxygen- and/or nitrogen-containing ring. "X" represents a keto group, methylene or hydroxymethyl. "R" represents hydrogen or methyl. "B" represents a polynuclear cyclic structure and may be biphenyl, bicyclohexyl, phenanthrene, or dihydrophenanthrene.

It is most preferred that "A" is an oxygen containing heterocyclic, and most preferably a 1,3-dioxane system. It is most preferred that "X" is a carbonyl group. Solubility properties of the compound may be changed by use of a tertiary amine wherein "R" equals hydrogen as opposed to a quaternary amine wherein "R" equals methyl. Both have their desired properties. The compound may be directly effective on the brain if the less water soluble tertiary amine moiety is used, i.e. "R" equals hydrogen. The most preferred compound so far produced is the compound having the following structure:

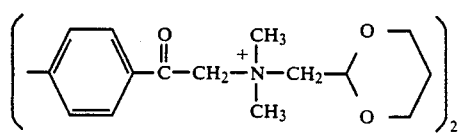

This compound, 4,4'-bis-[(1,3-dioxan-2-ylmethyl)amino-acetyl]biphenylDimethbromide, has a very high therapeutic ratio in comparison with reference drugs physostigmine and pyridostigmine.

These compounds, particularly compound (11) have been found to have a prophylactic effect. That is to say the compound can function in a preventative manner if administered prior to exposure to the gases. While it also may have post-exposure treatment effect, its greatest advantage may be its prophylactic properties. It is not known exactly how these compounds function as organophosphate antagonists, but it is believed that they may block ion passage channels in nerve membranes. This has been at least preliminarily observed by evidence that in frog skeletal muscles there appears to be a post-synaptic component which appears to involve ion channels.

The compounds of the present invention can be prepared by relatively standard procedures from 4,4'-bis-bromoacetylbiphenyl and the appropriate amine. 2-Dimethylaminomethyl-1-,3-dioxane was conveniently prepared in high yield in a one-step synthesis by acid-catalyzed transetherification of N,N-dimethylaminoacetaldehyde diethylacetal with propane-1,3-diol. Spectral (IR, NMR, MS) data on all intermediates and final compounds were consistent with the proposed structures. For further details see Cannon et al., *Pharm. Res.*, 5, 359 (1988).

The process of the present invention is a two-step addition process. In the first step the oxygen heterocyclic ring is prepared by a transetherification reaction with the propane 1,3-diol and dimethylaminoacetaldehyde diethylacetal. The reaction is run preferably in the presence of a non-polar inert hydrocarbon solvent such as benzene, toluene or cyclohexane. Preferably the reaction is run with acid catalysis by a small amount of sulfuric acid or paratoluene sulfonic acid. Temperature or pressure are not critical in this first reaction step. It can be run at reflux temperature conditions, i.e. within the range of about 80° C. to about 110° C.

The product of the first reaction step is isolated as illustrated in the Examples, and this product is then used in the second reaction step. In the second reaction step the product of the first reaction is permitted to react with 4,4'-bis bromoacetylbiphenyl to yield the reaction product of the invention. In the second reaction step, polar solvents such as acetonitrile or tetrohydrofuran are employed. This reaction can be run at room temperature. It is desired to use a slight excess (perhaps 5-15%) of the heterocyclic in the reaction.

In accordance with the present invention, as series of hemicholinium-3 congeners have been prepared, and for convenience hereinafter they are numbered 4-13. The structures of these are represented as follows:

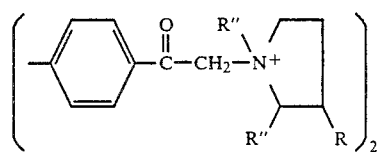

4  R = H; R' = R" = CH₃
5  R = R" = CH₃; R' = H
6  R = R' = H; R" = CH₃
7  R = R' = R" = CH₃

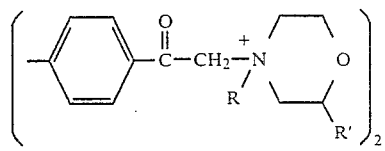

8  R = R' = H
9  R = CH₃; R' = H
10 R = R' = CH₃

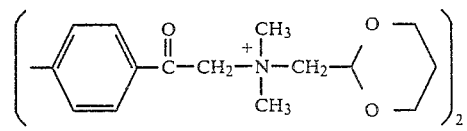

11

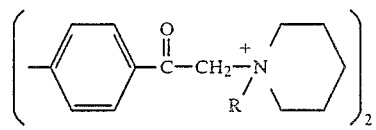

12 R = H
13 R = CH₃

Some of these include pyrrolidine systems (4-7); 1,4-oxazine systems (8-10); and 1,3-dioxane system (11), a cyclic acetal congener of 2b; and some piperidine derivatives (12, 13).

The following examples illustrate the preparation of the compounds (4-13), including the preferred compound (11), and present pharmacological data on their protective effects against paraoxon.

The dosage level of the compound will vary according to the weight of the mammal treated. Generally it can dosed by intraperitoneal injection. The tertiary amine compounds can be dosed orally, since these compounds have a favorable partition coefficient for absorption across the wall of the gut.

Generally speaking, the compounds may be delivered in suitable pharmaceutical preparations, either oral or injectable. They may be in liquid dosage form or solid tablet form.

When in unit dosage form suitable conventional pharmaceutical preparations can be used. Pharmaceutical carriers which are liquid or solid may be used. The preferred liquid carrier is water. Flavoring materials may be included in the solutions as desired.

Solid pharmaceutical carriers such as starch, sugar, talc, mannitol and the like may be used to form powders. Mannitol is the preferred solid carrier. The powders may be instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of one or more of the phenylalkylhydrazines, advisably as a non-toxic acid addition salt, and may be administered one or more at a time at regular intervals. Such unit dosage forms, however, should generally contain a concentration of 0.1% to 10% by weight of one or more of the active.

A typical tablet may have the composition:

|   | Mg. |
|---|---|
| 1. Active | 12.5 |
| 2. Mannitol | 100 |
| 3. Stearic acid | 3 |

A granulation is made form the mannitol. The other ingredients are added to the dry granulation and then the tablets are punched.

Another tablet may have the composition:

|   | Mg. |
|---|---|
| 1. Active | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   | Mg. |
|---|---|
| 1. Active | 5 |
| 2. Lactose U.S.P. | 200 |
| 3. Starch U.S.P. | 16 |
| 4. Talc U.S.P. | 8 |

The oral route is preferred for administering the active phenylalkylhydrazines.

Dosages of from about 1 mg. to 50 mg. may be administered to obtain the stated actives. However, the recommended dosages are from 3 to 12 mg. daily. Larger dosages may be administered on an interrupted schedule but generally not more than 50 mg., and preferably not more than 25 mg., is administered daily.

EXAMPLES OF PREPARATION OF COMPOUNDS (4–13)

4,4'-bis-(2-Methylpyrrolidinoacetyl)biphenyl Dimethbromide(4). 4,4'-bis-(Bromoacetyl)biphenyl (1.32 g, 0.0033 mol) and 0.99 g (0.01 mol) of 1,2-dimethylpyrrolidine in 70 mL of THF and 30 mL of MeOH were heated under reflux until all of the insoluble material dissolved; soon after, a yellowish white solid began to separate from the refluxing solvent. At this point, volatiles were removed from the reaction mixture under reduced pressure and the solid residue was recrystallized from MeOH-Me$_2$CO (1:2) to afford 1.6 g (81%) of a crystalline solid, mp 241° C. Anal. ($C_{28}H_{38}Br_2N_2O_2$) C, H, N.

4,4'-bis-(3-Methylpyrrolidinoacetyl)biphenyl Dimethbromide(5). This was prepared in 86% yield using 1,3-dimethylpyrrolidine by the method described for 4, mp 245°–246° C. Anal. ($C_{28}H_{38}Br_2N_2O_2$) C, H, N.

2-Dimethylaminomethyl-1,3-dioxan(14). A mixture of 16.1 g (0.1 mol) of N,N-dimethylaminoacetaldehyde diethylacetal, 8.36 g (0.11 mol) of propane-1,3-diol, and 12 mL of conc HCl was subjected to slow distillation until the theoretical volume of EtOH was collected. The reaction mixture was neutralized with saturated Na$_2$CO$_3$ and then was extracted with three 30 mL portions of Et$_2$O. The pooled extracts were dried (Na$_2$SO$_4$), filtered, and volatiles were removed from the filtrate under reduced pressure. The liquid residue was distilled, bp 40° C. (2.5 mm) to afford 10.15 g (70%) of product. This was characterized as its HCl salt, mp 168°–169° C. (from MeOH). Anal. ($C_8H_{16}ClNO_2$) C, H, N.

4,4'-bis-[(1,3-dioxan-2-ylmethyl)aminoacetyl]biphenyl Dimethbromide(11). Compound 14 (1.45 g, 0.01 mol) and 1.32 g (0.0033 mol) of 4,4'-bis-bromoacetylbiphenyl were stirred at room temperature in 50 mL of MeCN-H$_2$O(4:1) until all of the insoluble material dissolved. Volatiles were then removed under reduced pressure and the solid residue was recrystallized from 2-PrOH—H$_2$O to yield 1.75 g (77%) of product, mp 289° C. (dec). Anal. ($C_{28}H_{38}Br_2N_2O_6$) C, H, N.

4,4'-bis-(Tetrahydro-1,4-oxazin-4-ylacetyl)biphenyl Dihydrochloride(8). 4,4'-bis-Bromoacetylbiphenyl (1.32 g, 0.0033 mol) and 0.87 g (0.01 mol) of tetrahydro-1,4-oxazine were stirred in 50 mL of MeCN until all insoluble material dissolved. Volatiles were removed under reduced pressure and the residue was taken up in 25 mL of H$_2$O and this solution was treated with excess Na$_2$CO$_3$. The resulting yellow solid was collected on a filter and air dried. A solution in MeOH was treated with anhydrous HCl and the resulting solid was recrystallized from 2-PrOH—H$_2$O (1:1) to yield 1.4 g (83%) of a white solid, mp 289° C. (dec). Anal. ($C_{24}H_{30}Cl_2N_2O_4$) C, H, N.

4,4'-bis-(Tetrahydro-1,4-oxazin-4-ylacetyl)biphenyl Dimethbromide(9). 4,4'-bis-Bromacetylbiphenyl (1.31 g, 0.0033 mol) and 1.01 g (0.01 mol) of 4-methyltetrahydro-1,4-oxazine were treated as described for 11. The product (1.7 g, 86%) was recrystallized from 2-PrOH—H$_2$O, mp 261° C. (dec). Anal. ($C_{26}H_{34}Br_2N_2O_4$) C, H, N.

4,4'-bis-(2-Methyltetrahydro-1,4-oxazine-4-ylacetyl)-biphenyl Dimethbromide(10). To an ice-H$_2$O-chilled solution of 10.1 g (0.1 mol) of 2-methyltetrahydro-1,4-oxazine in 11 mL of 37% aqueous formaldehyde solution (0.135 mol) was added dropwise and with stirring 8.5 mL of 95% formic acid (0.25 mol). After addition was complete, the reaction mixture was heated under reflux for 24 hours. It was then brought to room temperature and 15 mL of conc HCl was added. The resulting mixture was extracted with Et$_2$O, and the pH of the aqueous phase was adjusted to 12 (pH paper) with 20% NaOH. It was then extracted with 500 mL of Et$_2$O for 24 hours in a liquid-liquid extractor. The ethereal extract was dried (Na$_2$SO$_4$) and volatiles were removed under reduced pressure to afford 7.8 g (68%) of 2,4-dimethyltetrahydro-1,4-oxazine which was used in the next step without further purification. A 1.5 g (0.01 mol) portion of this tertiary amine and 1.32 g (0.0033 mol) of 4,4'-bis-bromacetylbiphenyl were stirred at room temperature in 50 mL of MeCN—H$_2$O (4:1) until all solid material dissolved (approx. 4 hours). Volatiles were then removed under reduced pressure and the solid residue was recrystallized from EtOH to yield 1.83 g (89%) of product, mp 217° C. (dec). Anal. ($C_{18}H_{38}Br_2N_2O_4$) C, H, N.

4,4'-bis-(Pyrrolidinoacetyl)biphenyl Dimethbromide(6). N-Methylpyrrolidine (0.85 g, 0.01 mol) and 1.32 g (0.0033 mol) of 4,4'-bis-bromoacetylbiphenyl in 70 mL of THF and 30 mL of MeOH were treated as described for (4). The crude product was recrystallized from EtOH to yield 1.56 G (84%) of material, mp 288°-289° C. Anal. ($C_{26}H_{34}Br_2N_2O_2$) C, H, N.

4,4'-bis-(Piperidinoacetyl)biphenyl Dihydrobromide (12). 4,4-bis-Bromacetylbiphenyl (1.32 g, 0.0033 mol) and 1.13 g (0.013 mol) of piperidine were stirred at room temperature in 70 mL of THF and 30 mL of MeOH until a clear solution resulted (approx. 30 min.) Anhydrous HBr was passed through this solution until a solid separated. This material was collected on a filter and was recrystallized from EtOH to yield 1.52 g (82%) of product, mp 301° C. (dec). Anal. ($C_{26}H_{34}Br_2N_2O_2$) C, H, N.

4,4'-bis-(Piperidinoacetyl)biphenyl Dimethbromide(13). A mixture of 2.64 g (0.0067 mol) of 4,4'-bis-bromacetylbiphenyl and 1.98 g (0.02 mol) of N-methylpiperidine in 70 mL of THF and 30 mL of MeOH was stirred at room temperature until all suspended solid material dissolved. Volatiles were then evaporated under reduced pressure and the residue was recrystallized from EtOH to afford 3.6 g (90%) of product, mp 246° C. (dec). Anal. ($C_{28}H_{38}Br_2N_2O_2$) C, H, N.

4,4'-bis-(Pyrrolidinoacetyl)biphenyl Dihydrobomide(7). A mixture of 1.32 g (0.0033 mol) of 4,4'-bis-bromoacetylbiphenyl and 0.52 g (0.0073 mol) of pyrrolidine in 70 mL of THF and 30 mL of MeOH was stirred at room temperature until all solid material dissolved (approx. 0.5 hours). Anhydrous HBr was bubbled through the reaction solution; the resulting mixture was cooled in an ice bath, and the white solid which separated was collected on a filter. This was crystallized twice from EtOH to afford 1.48 g (83%) of product, mp 306° C. (dec). Anal. ($C_{24}H_{30}Br_2N_2O_2$) C, H, N.

EXAMPLES SHOWING PHARMACOLOGICAL DATA

Inhibition of neuromuscular transmission was determined as described by Benz and Long (Benz, F. W. and Long, J. P., *J. Pharmacol. Exp. Ther.*, 128, 231 (1986)). Dutch rabbits weighing 1.5-2.0 kg were anesthetized with 250 mg/kg of phenobarbital Na administered intravenously (IV). The trachea was isolated and respiration was supported by a Harvard respiration pump. The jugular vein was cannulated for IV administration of drugs. One of the sciatic nerves was isolated, sectioned centrally, and bipolar Ag electrodes were placed on the distal end of the sciatic nerve and were attached to a Grass S4C stimulator. The ankle was attached to a solid mount and the tendon of Achilles was isolated and sectioned. Ten gram resting tension was applied to the tendon and contractions were recorded using a Beckman R-611 recorder. The following parameters of stimulations were used: every 10 sec. interrupted tetanic stimulation was delivered for 0.2 sec. at 200 Hz. The pulse duration was 0.2 msec, and maximal voltage was applied (usually 20 V). Antagonistic properties of intravenous choline chloride (5 mg/kg) were evaluated.

In order to understand the effectiveness of these compounds on antagonism of insecticides, the compounds were studied as antagonists of the brand Paraoxon induced toxicity in mice. The compounds were compared against physostigmine and pyridostigmine, commercially available phototypical protective agents as standards.

Mice weighing 18-22 g were used to evaluate the protective efficacy of the compounds. First, the $LD_{50}$ dose (IM) of an experimental compound was determined, then fractional doses (varied by 0.3 log units) of the $LD_{50}$ were assayed. The assay for protective activity was conducted as follows: (1) the dose-ratio of the $LD_{50}$ was administered IM into the left handlimb; (2) either 30 or 120 min. later, $3 \times LD_{50}$ dose of paraoxon was administered sc. followed immediately by 11.2 mg/kg of atropine sulfate administered IM into the right hindlimb. The mice were observed for 24 hours. In this experimental procedure using saline solution, the dose of the brand Paraoxon was regarded as $LD_{99}$. With this experimental procedure information was obtained concerning behavioral responses of experimental compounds alone and concerning interactive responses with paraoxon duration of action, protective dose 50 ($PD_{50}$), and therapeutic index (TI). The TI was calculated by the formula $LD_{50}/PD_{50}$.

Table 1 shows the activity of the subject compounds, evaluated for their ability to inhibit neuromuscular transmission. Compounds 4 and 6 are potent inhibitors of neuromuscular transmission, and since choline is an effective antagonist, the mechanism of their action probably involves inhibition of choline transport, similar to hemicholinium-3. Several of the agents (6,9,10,11,13) produced "cholinergic" responses, probably by inhibition of acetylcholinesterase.

TABLE 1

| Inhibition of Rabbit Neuromuscular Transmission | |
|---|---|
| Compound | $ID_{50}\mu$mol/kg (95% C.L.) |
| 4 | 0.057 (0.04–0.08) |
| 5 | 0.21 (0.02–0.03) |
| 6 | 0.07 (0.03–0.3) |
| 7 | inactive to 5.6 |
| 8 | inactive to 2.08 |
| 9 | 0.58 (0.26–2.5) |
| 10 | inactive to 0.16 |
| 11 | 0.34 (0.14–4.8) |
| 12 | inactive to 1.8 |
| 13 | 0.11 (0.03–0.4) |

Table 2 shows the $LD_{50}$ values of the compounds and their ability to protect mice against Paraoxon-induced lethality. Only compounds 10, 11, and 13 were capable of producing at least 50% survival. Compounds 10 and 13 were only moderately effective. Compound 11 is a very effective antagonist of the brand Paraoxon induced toxicity, with an $ED_{50}$ of 13 µg/kg.

TABLE 2

Toxicity and Antagonistic Activity Against Paraoxon in Mice

| | | % of mice surviving pretreatment time fraction of $LD_{50}$ dose | | | | | | | | | | | |
|---|---|---|---|---|---|---|---|---|---|---|---|---|---|
| | | 0.5 hr | | | | | | | | | 2.0 hr | | |
| Compound | $LD_{50}$ µmole/kg | ¼ | ⅛ | 1/16 | 1/32 | 1/64 | 1/128 | 1/256 | 1/512 | ¼ | ⅛ | 1/16 | 1/32 |
| 4 | 0.67 | 0 | | | | | | | | 0 | | | |
| 5 | 0.84 | 25 | | | | | | | | | | | |
| 6 | 0.74 | 0 | | | | | | | | 0 | | | |
| 7 | 743.5 | 0 | | | | | | | | 0 | | | |

TABLE 2-continued

Toxicity and Antagonistic Activity Against Paraoxon in Mice

| | | % of mice surviving pretreatment time fraction of $LD_{50}$ dose | | | | | | | | | | |
|---|---|---|---|---|---|---|---|---|---|---|---|---|
| | | 0.5 hr | | | | | | | | 2.0 hr | | |
| Compound | $LD_{50}$ μmole/kg | ¼ | ⅛ | 1/16 | 1/32 | 1/64 | 1/128 | 1/256 | 1/512 | ¼ | ⅛ | 1/16 | 1/32 |
| 8 | no death to 2079 μmole/kg[a] | | | | | | | | | | | | |
| 9 | 3.8 | 25 | | | | | | | | 12 | | | |
| 10 | 13.0 | 63 | 88 | 0 | 0 | | | | | 0 | | | |
| 11 | 7.3 | 63 | 100 | 100 | 88 | 100 | 100 | 63 | 25 | 88 | 100 | 38 | 25 |
| 12 | 397.5 | 37 | | | | | | | | 0 | | | |
| 13 | 1.6 | 75 | 50 | 0 | | | | | | 0 | | | |

[a]Not tested for protective action against paraoxon.

Table 3 summarizes the activity of 11 and two reference compounds for protection against the brand Paraoxon-induced toxicity. Compound 11 shows dramatic antagonistic actions against paraoxon; however, its mechanism of antagonistic action is unknown. Studies in rabbits suggest that 11 is a weak inhibitor of choline transport, and it is possibly an inhibitor of acetylcholinesterase. Postjunctional activity of 11 has yet to be described. It is possible that optimal efficacy against organophosphate-induced toxicity will be realized with compounds exhibiting multi-mechanisms.

TABLE 3

Relative Activity of Three Potent Antagonists of Paraoxon-Induced Toxicity in Mice

| Compound | $LD_{50}$ μmol/kg | Protection vs. Paraoxon $ED_{50}$ mol/kg | Therapeutic Index |
|---|---|---|---|
| physostigmine | 1.2 | 0.02 | 60 |
| pyridostigmine | 10.3 | 1.3 | 8 |
| 11 | 7.3 | 0.02 | 360 |

It can be seen that each of the compounds of the present invention, as illustrated, function effectively as antagonists of the brand Paraoxon-induced toxicity in mice. The therapeutic index of (11) is far superior to the commercially known antagonists, indicating a high safety level.

What is claimed is:

1. A compound of the formula:

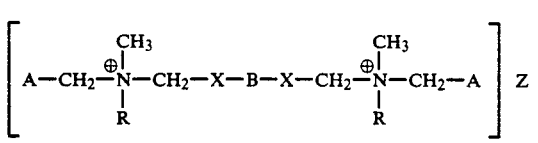

wherein "A" is a dioxan ring; "R" is selected from the group consisting of hydrogen and methyl; "X" is selected from the group consisting of keto, methylene and hydroxymethylene; "B" is a biphenyl ring; and Z represents a suitable number of counterbalancing halide anions.

2. A compound of claim 1 wherein 37 X" is a keto.
3. A compound of claim 1 wherein "R" is methyl.
4. 4,4'-bis-[[(1,3-dioxan-2-ylmethyl)methylamino]acetyl]biphenyl Dimethbromide.
5. A composition for use as an antagonist for organophosphate induced toxicity, comprising:
a small but antagonistic effective amount of a compound of the formula:

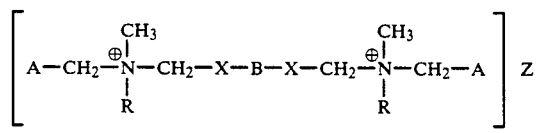

wherein "A" is a dioxan ring; "R" is selected from the group consisting of hydrogen and methyl; "X" is selected from the group consisting of keto, methylene and hydroxymethylene; "B" is a biphenyl ring; and Z represents a suitable number of counterbalancing halide anions; and
a pharmaceutically acceptable carrier.

6. A composition of claim 5 wherein the compound is 4,4'-bis-[[(1,3-dioxan-2-ylmethyl)methylamino]acetyl]biphenyl Dimethbromide.
7. A composition of claim 5 wherein the dosage amount is from about 1 mg to about 50 mg.
8. A method of prophylactically inhibiting organophosphate toxicity, comprising:
administering to a mammal a small but antagonistic effective amount of a compound of the formula:

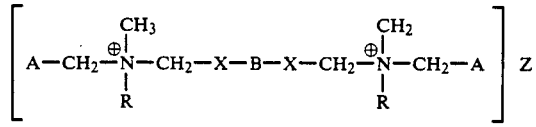

wherein "A" is a dioxan ring; "R" is selected from the group consisting of hydrogen and methyl; "X" is selected from the group consisting of keto, methylene and hydroxymethylene; "B" is a biphenyl ring; and Z represents a suitable number of counterbalancing halide anions.

9. The method of claim 8 wherein the compound is 4,4'-bis-[[(1,3-dioxan-2-ylmethyl)methylamino]acetyl]biphenyl Dimethbromide.

* * * * *